United States Patent
Kelley et al.

(10) Patent No.: US 8,530,193 B2
(45) Date of Patent: Sep. 10, 2013

(54) ALTERING ENZYME BALANCE THROUGH FERMENTATION CONDITIONS

(75) Inventors: Aaron Kelley, Fremont, CA (US); Chuanbin Liu, Mountain View, CA (US); Colin Mitchinson, Half Moon Bay, CA (US)

(73) Assignee: Danisco US Inc., Palo Alto, CA (US)

( * ) Notice: Subject to any disclaimer, the term of this patent is extended or adjusted under 35 U.S.C. 154(b) by 5 days.

(21) Appl. No.: 13/264,905

(22) PCT Filed: Apr. 30, 2010

(86) PCT No.: PCT/US2010/033125
§ 371 (c)(1), (2), (4) Date: Nov. 23, 2011

(87) PCT Pub. No.: WO2010/127219
PCT Pub. Date: Nov. 4, 2010

(65) Prior Publication Data
US 2012/0064579 A1    Mar. 15, 2012

Related U.S. Application Data

(60) Provisional application No. 61/174,460, filed on Apr. 30, 2009.

(51) Int. Cl.
*C12P 19/00*    (2006.01)
*C12N 9/00*    (2006.01)

(52) U.S. Cl.
USPC ............... 435/72; 435/96; 435/183; 435/209

(58) Field of Classification Search
None
See application file for complete search history.

(56) References Cited

FOREIGN PATENT DOCUMENTS
WO    WO 2004/035070    *    4/2004
WO    WO 2008/008070    *    1/2008

* cited by examiner

*Primary Examiner* — Nashaat Nashed
(74) *Attorney, Agent, or Firm* — Danisco US Inc.

(57) ABSTRACT

This present disclosure relates to methods for improved production of proteins from a cell culture, particularly to culture components and conditions that can preferentially increase the expression of proteins produced from genes under the control of xylanase gene promoter sequences. The improved methods can be used for the production of enzyme compositions with enhanced xylanase and hemicellulolytic activity.

20 Claims, No Drawings

SEQUENCE LISTING

<160> NUMBER OF SEQ ID NOS: 2

<210> SEQ ID NO 1
<211> LENGTH: 222
<212> TYPE: PRT
<213> ORGANISM: Trichoderma reesei

<400> SEQUENCE: 1

Met Val Ser Phe Thr Ser Leu Leu Ala Ala Ser Pro Pro Ser Arg Ala
1               5                   10                  15

Ser Cys Arg Pro Ala Ala Glu Val Glu Ser Val Ala Val Glu Lys Arg
            20                  25                  30

Gln Thr Ile Gln Pro Gly Thr Gly Tyr Asn Asn Gly Tyr Phe Tyr Ser
        35                  40                  45

Tyr Trp Asn Asp Gly His Gly Gly Val Thr Tyr Thr Asn Gly Pro Gly
    50                  55                  60

Gly Gln Phe Ser Val Asn Trp Ser Asn Ser Gly Asn Phe Val Gly Gly
65                  70                  75                  80

Lys Gly Trp Gln Pro Gly Thr Lys Asn Lys Val Ile Asn Phe Ser Gly
                85                  90                  95

Ser Tyr Asn Pro Asn Gly Asn Ser Tyr Leu Ser Val Tyr Gly Trp Ser
            100                 105                 110

Arg Asn Pro Leu Ile Glu Tyr Tyr Ile Val Glu Asn Phe Gly Thr Tyr
        115                 120                 125

Asn Pro Ser Thr Gly Ala Thr Lys Leu Gly Glu Val Thr Ser Asp Gly
    130                 135                 140

Ser Val Tyr Asp Ile Tyr Arg Thr Gln Arg Val Asn Gln Pro Ser Ile
145                 150                 155                 160

Ile Gly Thr Ala Thr Phe Tyr Gln Tyr Trp Ser Val Arg Arg Asn His
                165                 170                 175

Arg Ser Ser Gly Ser Val Asn Thr Ala Asn His Phe Asn Ala Trp Ala
            180                 185                 190

Gln Gln Gly Leu Thr Leu Gly Thr Met Asp Tyr Gln Ile Val Ala Val
        195                 200                 205

Glu Gly Tyr Phe Ser Ser Gly Ser Ala Ser Ile Thr Val Ser
    210                 215                 220

<210> SEQ ID NO 2
<211> LENGTH: 347
<212> TYPE: PRT
<213> ORGANISM: Trichoderma reesei

<400> SEQUENCE: 2

Met Lys Ala Asn Val Ile Leu Cys Leu Leu Ala Pro Leu Val Ala Ala
1               5                   10                  15

-continued

```
Leu Pro Thr Glu Thr Ile His Leu Asp Pro Glu Leu Ala Ala Leu Arg
            20              25              30

Ala Asn Leu Thr Glu Arg Thr Ala Asp Leu Trp Asp Arg Gln Ala Ser
        35              40              45

Gln Ser Ile Asp Gln Leu Ile Lys Arg Lys Gly Lys Leu Tyr Phe Gly
    50              55              60

Thr Ala Thr Asp Arg Gly Leu Leu Gln Arg Glu Lys Asn Ala Ala Ile
65              70              75              80

Ile Gln Ala Asp Leu Gly Gln Val Thr Pro Glu Asn Ser Met Lys Trp
                85              90              95

Gln Ser Leu Glu Asn Asn Gln Gly Gln Leu Asn Trp Gly Asp Ala Asp
            100             105             110

Tyr Leu Val Asn Phe Ala Gln Gln Asn Gly Lys Ser Ile Arg Gly His
        115             120             125

Thr Leu Ile Trp His Ser Gln Leu Pro Ala Trp Val Asn Asn Ile Asn
    130             135             140

Asn Ala Asp Thr Leu Arg Gln Val Ile Arg Thr His Val Ser Thr Val
145             150             155             160

Val Gly Arg Tyr Lys Gly Lys Ile Arg Ala Trp Asp Val Val Asn Glu
                165             170             175

Ile Phe Asn Glu Asp Gly Thr Leu Arg Ser Ser Val Phe Ser Arg Leu
            180             185             190

Leu Gly Glu Glu Phe Val Ser Ile Ala Phe Arg Ala Ala Arg Asp Ala
        195             200             205

Asp Pro Ser Ala Arg Leu Tyr Ile Asn Asp Tyr Asn Leu Asp Arg Ala
    210             215             220

Asn Tyr Gly Lys Val Asn Gly Leu Lys Thr Tyr Val Ser Lys Trp Ile
225             230             235             240

Ser Gln Gly Val Pro Ile Asp Gly Ile Gly Ser Gln Ser His Leu Ser
                245             250             255

Gly Gly Gly Gly Ser Gly Thr Leu Gly Ala Leu Gln Gln Leu Ala Thr
            260             265             270

Val Pro Val Thr Glu Leu Ala Ile Thr Glu Leu Asp Ile Gln Gly Ala
        275             280             285

Pro Thr Thr Asp Tyr Thr Gln Val Val Gln Ala Cys Leu Ser Val Ser
    290             295             300

Lys Cys Val Gly Ile Thr Val Trp Gly Ile Ser Asp Lys Asp Ser Trp
305             310             315             320

Arg Ala Ser Thr Asn Pro Leu Leu Phe Asp Ala Asn Phe Asn Pro Lys
                325             330             335

Pro Ala Tyr Asn Ser Ile Val Gly Ile Leu Gln
            340             345
```

ALTERING ENZYME BALANCE THROUGH FERMENTATION CONDITIONS

I. CROSS REFERENCE TO RELATED APPLICATIONS

This application claims priority under 35 U.S.C. §371 to International Application No. PCT/US2010/0333125, filed Apr. 30, 2010, which claims benefit to U.S. Provisional Application No. 61/174,460 filed Apr. 30, 2009 both of which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "31086US2_SEQLIST", created on Sep. 29, 2011, which is 5,347 bytes in size.

II. TECHNICAL FIELD

This present teachings relate to methods for improved production of proteins from a cell culture, particularly to culture components and conditions that can preferentially increase the expression of proteins produced from genes under the control of xylanase gene promoter sequences. The improved methods can be used for the production of cellulase compositions with enhanced xylanase and hemicellulolytic activity.

III. INTRODUCTION

The principal components of biomass are cellulose and hemicellulose. Cellulose consists of polymers of β-1,4-linked glucose residues that are organized into higher order fibrillar structures. Xylans are almost as ubiquitous as cellulose in plant-cell walls and contain predominantly β-D-xylose units linked as in cellulose. Some xylans contain other sugars, such as L-arabinose, but they form branches and are not part of the main chain.

Cellulose and hemicellulose can be converted into sugars, such as glucose, and used as an energy source by numerous microorganisms including bacteria, yeast and fungi for industrial purposes. Cellulosic materials can also be converted into sugars by commercially available enzymes, and the resulting sugars can be used as a feedstock for industrial microorganisms to produce products such as plastics and ethanol. The filamentous fungus, *Trichoderma reesei*, is an efficient producer of cellulase enzymes. As such *Trichoderma reesei* has been exploited for its ability to produce these enzymes. However, current cellulase products generally lack the ability to completely hydrolyze hemicellulosic materials, some of which remain unconsumed in the biomass compositions and may interfere with the handling and disposal of the biomass.

The cellulolytic mix of *Trichoderma reesei* proteins is among the best characterized cellulolytic pathways of microorganisms. The cellulases that comprise these mixes are classified into two broad categories: the endoglucanases (EG) and the cellobiohydrolases (CBH). β-glucosidase (BGL) is also part of the cellulase mix of *Trichoderma reesei*.

Expression of the genes comprising the cellulase system is coordinate and regulated at the transcriptional level. The members of this system act synergistically, and as noted above, are necessary for the efficient hydrolysis of cellulose to soluble oligosaccharides.

Expression and production of the main cellulase genes (cbh1, cbh2, egl1, and egl2) and xylanase genes (xyn1, xyn2, and xyn3) in *Trichoderma* are dependent on the carbon source available for growth. The cellulase genes are tightly repressed by glucose and can be induced several thousand fold by cellulose or the disaccharide sophorose. Indeed, the expression level of the major cellobiohydrolase 1 (CBH1) is up-regulated several thousand fold on media containing inducing carbon sources such as cellulose or sophorose compared with glucose containing media (Ilmen et al., App. Environ. Microbio., 1298-1306, 1997).

The three major forms of xylanase (xyn1, xyn2 and xyn3) are not co-regulated. Research has shown that the expression of xyn1 and xyn2 are regulated in such different manners that xyn1 is induced in the presence of xylan and xylose and slightly by sophorose, whereas xyn2 is rather nonspecifically affected by both xylanase and cellulase inducers (Zeilinger, et al. 1996; March et al. 1996, Xu, et al. 1998) The third xylanase, xyn3, is not induced at all by xylan, the substrate for this enzyme, but rather it is induced by cellulose and its derivatives. (Xu, et al., *Appl Microbiol Biotechnol.* 2000. 54:370-375, Furukawa, *Fungal Genetics and Biology.* 2008. 45:1094-1102). Further, high concentrations of glucose are known to repress expression of xyn1. Thus, the present disclosure represents a surprising discovery that processed glucose plus xylose induced both cellulase and xylanase expression even though both glucose and xylose are known in the art to discourage cellulase and xylanase activity.

Current mixed cellulase products lack an optimized system for hydrolyzing hemicellulosic materials. What is needed is the coproduction or blending of an optimized set of enzymes that are capable of degrading both the cellulosic and hemicellulosic components of biomass substrate. A further need exists for a commercially practical method for generating a balanced mixture of cellulase and xylanase enzymes.

IV. SUMMARY

It has now been discovered that incubation of a transglycosylating enzyme in a concentrated glucose solution at elevated temperature generates a processed glucose solution that when combined with a pentose, such as xylose, yields a mixed saccharide composition capable of inducing expression of a balanced cellulolytic and hemicellulolytic enzyme blend. Surprisingly, the resulting mixed saccharide composition is sufficient to induce cellulase and xylanase production as is without further purification. This discovery is surprising since glucose acts as a repressor of cellulase and certain xylanase genes in *Trichoderma reesei*. This discovery provides an inducer of cellulase and hemicellulase gene expression that is an inexpensive alternative to purified saccharide inducers and separate production of cellulase and xylanase enzymes.

One aspect of the present teachings provides methods for preparing a mixed saccharide composition, said method comprising (a) mixing a glucose solution with a transglycosylating enzyme to give an enzyme-glucose mixture; (b) incubating the enzyme-glucose mixture at an elevated temperature for a time sufficient to give a processed glucose mixture comprising at least one oligosaccharide; and (c) mixing the processed glucose mixture with a pentose to yield the mixed saccharide composition.

Another aspect of the present disclosure provides methods for preparing an enzyme composition, comprising (a) mixing a glucose solution with a transglycosylating enzyme to give an enzyme-glucose mixture; (b) incubating the enzyme-glucose mixture at an elevated temperature for a time sufficient to give a processed glucose mixture comprising at least one oligosaccharide; (c) mixing the processed glucose mixture with a pentose to yield a mixed saccharide composition; and (d) exposing a filamentous fungi to the mixed saccharide composition under conditions conducive to protein expression to generate the enzyme composition. Preferably the enzyme composition comprises 70% to 98% cellulase and 2% to 30% xylanase. In certain implementations, the conditions conducive to protein expression comprise a temperature between about 25° C. and about 30° C. In other implementations, the conditions conducive to protein expression comprise acidic conditions, particularly a pH between about 4.0 and about 6.0, more particularly at a pH between about 4.4 and about 5.5, most particularly between about pH 4.8 and about pH 5.5.

In certain implementations, the glucose solution comprises from about 5% to about 75% (wt/wt), more preferably from about 50% to about 75% (wt/t), glucose. The transglycosylating enzyme can be an enzyme classified in EC 2.4 or an enzyme classified in E.C. 3.2. In a preferred embodiment, the transglycosylating enzyme is a β-glucosidase or an endoglucanase.

In certain implementations, the elevated temperature is from about 50° C. to about 75° C. The enzyme-glucose mixture can incubated for between 8 hours and 500 hours, more preferably for between 48 hours and 72 hours. In a preferred implementation, the added pentose is xylose, more preferably added to a final concentration from about 1 g/L to about 50 g/L in the mixed saccharide composition. More preferably, the concentration of xylose in the mixed saccharide composition is from about 5 g/L to about 20 g/L. In one implementation, the pentose is black liquor.

Another aspect of the present disclosure provides an enzyme composition comprising, made by, or obtainable by mixing: (a) one or more xylanase enzyme(s) wherein at least one of said one or more xylanase enzyme(s) is a XYN2, or a XYN3; and one or more cellulase enzyme(s) wherein at least one of said one or more more cellulase enzyme(s) is a CBH1, CBH2 or a BGL1; wherein said enzyme composition comprises a ratio of a about 0.5 to about 1.0 xylanases to cellulases (w/w) or a ratio of about 0.05 to about 1.5 xylanase to CBH1 (w/w).

Other aspects of the present teaching provide mixed saccharide compositions produced according to the methods disclosed herein, an enzyme composition produced according to the methods disclosed herein and methods of degrading a biomass comprising contacting the biomass with an enzyme composition produced according to the methods disclosed herein.

These and other features of the present teachings are described herein.

V. DESCRIPTION OF VARIOUS EMBODIMENTS

It is to be understood that both the foregoing general description and the following detailed description are exemplary and explanatory only and are not restrictive of the compositions and methods described herein. Unless defined otherwise herein, all technical and scientific terms used herein have the same meaning as commonly understood by one of ordinary skill in the art to which this invention belongs. In this application, the use of the singular includes the plural unless specifically stated otherwise. The use of "or" means "and/or" unless state otherwise. Likewise, the terms "comprise," "comprising," "comprises," "include," "including" and "includes" are not intended to be limiting. All patents and publications, including all amino acid and nucleotide sequences disclosed within such patents and publications, referred to herein are expressly incorporated by reference.

The headings provided herein are not limitations of the various aspects or embodiments of the invention which can be had by reference to the specification as a whole. Accordingly, the terms herein are more fully defined by reference to the specification as a whole.

A. DEFINITIONS

As used herein, the following definitions shall apply unless otherwise indicated.

As used herein, the term "xylanase(s)" refers to a protein or polypeptide domain of a protein or polypeptide derived from a microorganism, e.g., a fungus, bacterium, or from a plant or animal, and that has the ability to catalyze cleavage of xylan, including branched xylans and xylooligosaccharides, at one or more of various positions of xylan's carbohydrate backbone. For the present disclosure, preferably, the xylanase is endo-1,4-β-xylanase (E.C. 3.2.1.8). In some embodiments, the xylanase is a beta-xylosidase or xylan 1,4-beta-xylosidase or 1,4-beta-D-xylan xylohydrolase or xylobiase or exo-1,4-β-xylosidase (EC 3.2.1.37) including enzymes that hydrolyze successive D-xylose residues from the non-reducing terminus of xylan polymers. Numerous xylanases from fungal and bacterial microorganisms have been identified and characterized. (See, e.g., U.S. Pat. No. 5,437,992; Coughlin, M. P. supra; Biely, P. et al., Proceedings of the second TRICEL symposium on *Trichoderma reesei* Cellulases and Other Hydrolases, Espoo 1993, P. Souminen and T. Reinikainen eds., Foundation for Biotechnical and Industrial Fermentation Research 8:125-135 (1993)). In particular, three specific xylanases (XYN1, XYN2, and XYN3) have been identified in I reesei (Tenkanen, et al., Enzyme Microb. Technol. 14:566 (1992); Torronen, et al., Bio/Technology 10:1461 (1992); and Xu, et al., Appl. Microbiol. Biotechnol. 49:718 (1998)). A fourth xylanase (XYN4) isolated from *T. reesei* is described in U.S. Pat. Nos. 6,555,335 and 6,768,001 to Saloheimo, et al., entitled "Xylanase from *Trichoderma reesei*, method for production thereof, and methods employing this enzyme," incorporated herein by reference in its entirety.

In some embodiments, XYN2 is a polypeptide comprising a sequence having at least 85%, at least 90%, at least 95%, at least 98%, at least 99% or 100% sequence identity to at least 50, at least 75, at least 100, at least 125, at least 150, at least 175, at least 200, at least 250, or at least 300 contiguous amino acid residues of positions 22 to 222 of: <u>mvsftsllaasppsrascrpaaevesvavekrqtiqpgtgynngyfysywnd ghggvtytngpggqfsvnwsnsgn</u> fvggkgwqpgtknkvinfsgsynpngnsylsvygwsrnplieyyivenfgtynpstgatklgevtsdgsvydiyrtqry nqpsiigtatfyqywsvrrnhrssgsvn-tanhhfnawaqqgltlgtmdyqivavegyfssgsasitvs (SEQ ID NO:1.) The signal sequence of XYN2 is underlined. The coding sequence can be found in Törrönen et al., 1992, Biotechnology 10:1461-65.

In some embodiments, XYN3 is a polypeptide comprising a sequence having at least 85%, at least 90%, at least 95%, at least 98%, at least 99% or 100% sequence identity to at least 50, at least 75, at least 100, at least 125, at least 150, at least 175, at least 200, at least 250, or at least 300 contiguous amino acid residues of positions 17 to 347 of: mkanvilcllaplvaalptetihldpelaalranltertadlwdrqasqsidqli <u>krkgklyfgtatdrglI</u> qreknaaiiqadlg qvtpensmkwqslennqgqlnwgdadylvnfaqqngksirghtliwhsqlpawvnninnad tlrqvirthvstv-vgry kgkirawdvvneifnedgtlrssvfsrllgeefvsia fraardadpsarly indynldranygkvnglktyvs kwisqgvpi dgigsqshlsggggsgtl-galqqlatvpvtelaiteldiqgapttdytqvvqaclsyskcv gitvwgisdkd-swrastnpllf danfnpkpaynsivgilq (SEQ ID NO:2). SEQ ID NO:42 is the sequence of the immature XYN3. Xyn3 has a predicted signal sequence corresponding to positions 1 to 16 of SEQ ID NO:2 (underlined); cleavage of the signal sequence is predicted to yield a mature protein having a sequence corresponding to positions 17 to 347 of SEQ ID NO:2.

"Oligosaccharide," as used herein, refers to a saccharide polymer containing a small number (typically three to ten) of component sugars (monosaccharides). Examples of monosaccharides include, but are not limited to, glucose, fructose, mannose, galactose, xylose, arabinose, and ribose. "Disaccharide," as used herein, refers to a sugar composed of two monomers.

"Glucose" is the most common sugar found in cellulose. As used herein, the term "glucose solution" refers to solution comprising the monosaccharide glucose, disaccharides or short oligomers, i.e., having 3 to 4 saccharides, containing at least one glucose unit. Exemplar oligomers that can be included in the glucose solution include, without limitation, cellobiose (a disaccharide consisting of two glucose molecules linked by a β(1→4) bond) and lactose (a disaccharide consisting of β-D-galactose and β-D-glucose linked by a β(1→4) bond).

As used herein, the term "pentose" includes crude, unrefined or unpurified compositions containing at least one pentose. Exemplary crude pentose compositions include, but are not limited to, black liquor form a xylitol plant, pulp plant, paper plant or other biorefinery.

"Cellulase," "cellulolvtic enzymes" or "cellulase enzymes" means bacterial or fungal exoglucanases or exo-cellobiohydrolases, and/or endoglucanases, and/or β-glucosidases. These three different types of cellulase enzymes act synergistically to convert cellulose and its derivatives to glucose.

As used herein, the term "transglycosylating enzyme" refers to a bacterial or fungal enzyme that acts as a catalyst for the transfer of a monosaccharide unit from a non-activated sugar, such as sucrose, lactose or starch, to an acceptor molecule, including but not limited to water and other sugar units. The result of glycosyl transfer can be a monosaccharide, an oligosaccharide, or a polysaccharide. Classical glycosyl transferase enzymes are classified in EC 2.4. Dextransucrase (EC 2.4.1.5) and cyclomaltodextrin glucanotransferase (EC 2.4.1.19) are representative classical glycosyl transferase enzymes capable of transferring a glucose unit. Additionally certain enzymes classified in EC 3.2, when presented with an excess of monosaccharide, can catalyze transfer of a monosaccharide unit to an acceptor molecule, typically another saccharide. In excess, the presence of high concentrations of monosaccharide, the typical product of glycosidase (EC 3.2) activity, drives the glycosidase reaction in reverse, resulting in addition, rather than removal of monosaccharide units. Exemplar glycosidases that can function as a transglycosylating enzyme include, but are not limited to, β-glucosidase (EC 3.2.1.21) endo-glucanases (e.g., EC 3.2.1.71), β-xylosidases (EC 3.2.1.27) and xyloglucanases (3.2.1.151).

"Filamentous fungi" include all filamentous forms of the subdivision Eumycota and Oomycota. In some embodiments, the whole broth is prepared from a *Acremonium, Aspergillus, Chrysosporium, Emericella, Fusarium, Humicola, Mucor, Myceliophthora, Neurospora, Scytalidium, Thielavia, Tolypocladium,* or *Trichoderma* species or species derived therefrom.

An "inducer" is any compound that causes cells to produce larger amounts of enzymes or other substances than they would otherwise produce if the inducer was absent.

The terms "isolated" or "purified" as used herein refer to a nucleic acid or amino acid that is removed from at least one component with which it is naturally associated.

B. Methods

The filamentous fungus *Trichoderma reesei* is one of the most extensively studied cellulolytic organisms (reviewed e.g. by Nevalainen and Penttila, Mycota, 303-319, 1995). In industry, the cellulolytic enzymes of *Trichoderma* are used for many purposes including; production of fuel ethanol, paper, rayon, cellophane, detergents and fibers. Cellulase enzymes are also used to improve the nutritional value of animal feeds, and to facilitate the extraction of valuable components from plant cells (Mandels, Biochem. Soc. Trans., 414-16. 1985). Thus, these enzymes are of primary importance in the production of many useful products.

The production of cellulases and xylanases in *Trichoderma* is dependent on the carbon source available. Cellulose, lactose and the disaccharide sophorose, induce cellulase synthesis by *Trichoderma reesei*. Conversely, the presence of glucose results in tight repression of cellulase gene expression. Similarly, xylanases are also tightly regulated in *Trichoderma reesei*. Like cellulase, at least some xylanases are tightly repressed by glucose. Providing the appropriate inducer for industrial scale production is a major problematic factor contributing to the difficulty in concurrently producing a balanced mixture of cellulases and hemicellulases, particularly xylanase.

It has now been discovered that when a transglycosylating enzyme is incubated in a concentrated glucose solution at elevated temperature, and then later supplemented with xylose, a mixed saccharide composition capable of inducing both cellulase and xylanase production is made. The mixed saccharide composition has between about 2 and 25 g/L sophorose and between about 2 and 25 g/L xylose. In addition, the mixed saccharide composition can comprise between about 35 and 60 g/L gentiobiose. Surprisingly, the mixed saccharide composition made as described herein requires no additional purification. The composition is competent to induce cellulase and xylanase production as is. This discovery provides the inexpensive alternative to lactose or purified sophorose currently used by industry, as well as a less cumbersome alternative to solid cellulose for the production of proteins regulated by inducible promoters in a filamentous fungus. Further, the expressed enzyme composition contains a higher amount of xylanase activity as compared to the cellulase mixtures made according to current practices in the industry.

In an alternative method of producing the mixed saccharide composition, end fermentation broth (expressed cellulytic enzymes plus cells) may be added to a glucose solution (e.g., 20%). The presence of the cells does not affect sophorose formation. Thus, there is no need to use a purified or partially purified transglycosylating enzyme. The enzyme mixture present at the end of a fermentation may be used although whole cells and cell fragments are still present.

In one embodiment, the present teaching provides a mixed saccharide composition comprising a processed glucose solution and a pentose, such as xylose, that can be used in filamentous fungi to induce production a range of cellulytic enzymes, including one or more enzyme selected from the group consisting of an endoglucanase, a cellobiohydrolase, a β-glucosidase and a xylanase. In an embodiment the mixed saccharide composition induces cellulase enzyme and xylanase enzyme production by *Trichoderma reesei*. It is surprising that the solution is effective at inducing both cellulase and xylanase gene expression, since cellulase and xylanase genes are known to be repressed by the presence of glucose.

In one embodiment an inducing feed is made by preparing a sterile solution of 5%-75% (wt/wt) glucose. A transglycosylating enzyme is added to a sterile glucose solution. In some embodiments, the transglycosylating enzyme is β-glucosidase. In one aspect the β-glucosidase is added to a final activity in the enzyme-glucose solution of less than 200 IU/ml. In another aspect β-glucosidase activity in the enzyme-glucose solution is between 1.5 IU/ml and 200 IU/ml. The transglycosylating enzyme can be present as one or more component in a mixed cellulase composition. Typically a mixed cellulase composition is added to the sterile glucose solution to a final concentration of between 2 g and 20 g total protein/L. The final protein range may be as low as 0.5 g/L and as high as 50 g/L. The enzyme-glucose solution is incubated at 50° C.-75° C. In some embodiments, the enzyme-glucose solution is incubated between about 50° C. and about 65° C. The solution is incubated for between 8 hours and 7 days with mixing. In one embodiment the incubation period is greater than two days. In second embodiment the incubation period is two days. In third embodiment the incubation period is three days. The processed glucose solution is harvested, supplemented with xylose and used for fermentation feeding. Optionally, the processed glucose solution is sterilized prior to addition of filter sterilized enzyme solutions. At larger volumes, the combined glucose-enzyme solution can be continuously sterilized, e.g. through a heat exchanger at 135° C. for 2 minutes on the way to the incubation tank. The pentose can be added to the glucose and enzyme prior to or after incubation at elevated temperature.

Another aspect provides methods for preparing an enzyme composition, comprising (a) mixing a glucose solution with a transglycosylating enzyme to give an enzyme-glucose mixture; (b) incubating the enzyme-glucose mixture at an elevated temperature for a time sufficient to give a processed glucose mixture comprising at least one disaccharide or oligomer; (c) mixing the processed glucose mixture with a pentose to yield a mixed saccharide composition; and (d) exposing a filamentous fungi to the mixed saccharide composition under conditions conducive to protein expression to generate the enzyme composition. Preferably the enzyme composition comprises 80% to 98% cellulase and 2% to 20% xylanase. In certain implementations, the conditions conducive to protein expression comprise a temperature between about 25° C. and about 30° C. In other implementations, the conditions conducive to protein expression comprise acidic conditions, more particularly a pH between about 4.0 and about 6.0.

Fermentation procedures for production of cellulolytic enzymes are known per se in the art. For example, cellulase enzymes can be produced either by solid or submerged culture, including batch, fed-batch and continuous-flow processes.

Culturing is accomplished in a growth medium comprising an aqueous mineral salts medium, organic growth factors, the carbon and energy source material, molecular oxygen, and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation media.

The composition of the aqueous mineral medium can vary over a wide range, depending in part on the microorganism and substrate employed, as is known in the art. The mineral media should include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

The fermentation reaction is an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth, since the assimilation of the substrate and corresponding growth of the microorganisms, is, in part, a combustion process.

Although the aeration rate can vary over a considerable range, aeration generally is conducted at a rate which is in the range of about 0.5 to 10, preferably about 0.5 to 7, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time this is balanced by the fact that high atmospheric pressures do increase equipment and operating costs.

The fermentation temperature can vary somewhat, but for filamentous fungi such as *Trichoderma reesei* the temperature generally will be within the range of about 20° C. to 40° C., generally preferably in the range of about 25° C. to 34° C., depending on the strain of microorganism chosen.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. With filamentous fungi, the pH normally is within the range of about 2.5 to 8.0; with *Trichoderma reesei*, the pH normally is within the range of about 3.0 to 7.0. pH range preferences for certain microorganisms are dependent on the media employed to some extent, as well as the particular microorganism, and thus change somewhat with change in media as can be readily determined by those skilled in the art. In methods for expressing an enzyme composition according to the present disclosure, the pH preferably is between about 4.0 and about 6.0.

While the average retention time of the fermentation admixture in the fermentor can vary considerably, depending in part on the fermentation temperature and culture employed, generally it will be within the range of about 24 to 500 hours, preferably presently about 24 to 400 hours.

Preferably, the fermentation is conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily washed off. It may be a problem, however, in the case of non-water-soluble substrates, and require added product-treatment steps such as suitable washing steps.

As described above, the time to reach this level is not critical and may vary with the particular microorganism and fermentation process being conducted. However, it is well known in the art how to determine the carbon source concentration in the fermentation medium and whether or not the desired level of carbon source has been achieved.

Although the fermentation can be conducted as a batch or continuous operation, fed batch operation is much to be preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium to the fermentor.

Each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittance, or the like. The feed rates of the various materials can be varied so as to obtain as rapid a cell growth rate as possible, consistent with efficient utilization of the carbon and energy source, to obtain as high a yield of microorganism cells relative to substrate charge as possible.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though presently preferred is operation under 15 L Biolafitte (Saint-Germain-en-Laye, France).

The collection and purification of the cellulase and xylanase enzymes from the fermentation broth can also be done by procedures known per se in the art. The fermentation broth will generally contain cellular debris, including cells, various suspended solids and other biomass contaminants, as well as the desired cellulase and xylanase enzyme product, which are preferably removed from the fermentation broth by means known in the art.

Suitable processes for such removal include conventional solid-liquid separation techniques such as, e.g., centrifugation, filtration, dialysis, microfiltration, rotary vacuum filtration, or other known processes, to produce a cell-free filtrate. It may be preferable to further concentrate the fermentation broth or the cell-free filtrate prior to crystallization using techniques such as ultrafiltration, evaporation or precipitation.

Precipitating the proteinaceous components of the supernatant or filtrate may be accomplished by means of a salt, e.g., ammonium sulfate, followed by purification by a variety of chromatographic procedures, e.g., ion exchange chromatography, affinity chromatography or similar art recognized procedures.

Various species of filamentous fungi can be used as expression hosts. In some embodiments, the mixed saccharide composition is used to induce cellulase and xylanase production from *Aspergillus aculeatus, Aspergillus awamori, Aspergillus foetidus, Aspergillus japonicus, Aspergillus nidulans, Aspergillus niger*, or *Aspergillus oryzae*. In another aspect, the enzyme composition is prepared from *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum*. In another aspect, the enzyme composition is prepared from *Humicola insolens, Humicola lanuginosa, Mucor miehei, Myceliophthora thermophila, Neurospora crassa, Scytalidium thermophilum*, or *Thielavia terrestris*. In another aspect, the enzyme composition is prepared from a *Trichoderma harzianum, Trichoderma koningii, Trichoderma longibrachiatum, Trichoderma reesei* e.g., RL-P37 (Sheir-Neiss et al., Appl. Microbiol. Biotechnology, 20 (1984) pp. 46-53; Montenecourt B. S., Can., 1-20, 1987), QM9414 (ATCC No. 26921), NRRL 15709, ATCC 13631, 56764, 56466, 56767, or *Trichoderma viride* e.g., ATCC 32098 and 32086.

Filamentous fungi suitable for use in the methods described herein include, but are not limited to the following genera: *Aspergillus, Acremonium, Aureobasidium, Beauveria, Cephalosporium, Ceriporiopsis, Chaetomium paecilomyces, Chrysosporium, Claviceps, Cochiobolus, Cryptococcus, Cyathus, Endothia, Endothia mucor, Fusarium, Gilocladium, Humicola, Magnaporthe, Myceliophthora, Myrothecium, Mucor, Neurospora, Phanerochaete, Podospora, Paecilomyces, Pyricularia, Rhizomucor, Rhizopus, Schizophylum, Stagonospora, Talaromyces, Trichoderma, Thermomyces, Thermoascus, Thielavia, Tolypocladium, Trichophyton*, and *Trametes pleurotus*. In some embodiments, the filamentous fungi include, but are not limited to the following: *A. nidulans, A. niger, A. awomari, A. aculeatus, A. kawachi* e.g., NRRL 3112, ATCC 22342 (NRRL 3112), ATCC 44733, ATCC 14331 and strain UVK 143f, *A. oryzae*, e.g., ATCC 11490, *N. crassa, Trichoderma reesei*, e.g., NRRL 15709, ATCC 13631, 56764, 56765, 56466, 56767, and *Trichoderma viride*, e.g., ATCC 32098 and 32086. In a preferred implementation, the filamentous fungus is a *Trichoderma* species. A particularly preferred species and strain for use in the disclosed methods is *Trichoderma reesei* RutC30, which is available from the American Type Culture Collection as *Trichoderma reesei* ATCC 56765.

In a preferred embodiment, the microbial host is a member of the species of *Trichoderma, Humicola, Fusarium, Aspergillus, Streptomyces, Thermomonospora, Bacillus*, or *Cellulomonas*.

Another aspect provides methods for preparing an enzyme composition, comprising (a) mixing a glucose solution with a transglycosylating enzyme to give an enzyme-glucose mixture; (b) incubating the enzyme-glucose mixture at an elevated temperature for a time sufficient to give a processed glucose mixture comprising at least one disaccharide or oligomer; (c) mixing the processed glucose mixture with a pentose to yield a mixed saccharide composition; and (d) exposing a filamentous fungi to the mixed saccharide composition under conditions conducive to protein expression to generate the enzyme composition, wherein said enzyme composition comprises at least a 1.5-fold increase in xylanase as compared to an enzyme composition prepared without step c).

In some embodiments, the enzyme composition comprises at least a 1.5-fold, 2.0-fold, 2.5-fold, 3.0-fold, 3.5-fold, 4.0-fold 4.5-fold, 5.0-fold, 5.5-fold, 6.0-fold, 6.5-fold, 7.0-fold, 7.5-fold, 8.0-fold, 8.5-fold, 9.0-fold, 9.5-fold, 10.0-fold 10.5-fold, 11.0-fold, 11.5-fold, 12.0-fold, 12.5-fold, 13.0-fold, 13.5-fold, 14.0-fold, 14.5-fold, 15.0-fold increase in xylanase as compared to an enzyme composition prepared without step c).

In some embodiments, the enzyme composition comprises a ratio of about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50 xylanase to CBH1 (w/w). In some embodiments, the enzyme composition comprises a ratio of about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50 XYN2 to CBH1 (w/w). In some embodiments, the enzyme composition comprises a ratio of about 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50 XYN3 to CBH1 (w/w).

In some embodiments, the enzyme composition comprises a ratio of about 0.5, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50 xylanase to cellulases (w/w). In some embodiments, the enzyme composition comprises a ratio of about 0.5, 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50 xylanase to CBH1, CBH2 and BGL1.

In another aspect, provided herein is an enzyme composition comprising, made by, or obtainable by mixing: (a) one or more xylanase enzyme(s) wherein at least one of said one or more xylanase enzyme(s) is a Xyn2, or a Xyn3; and (b) one or more cellulase enzyme(s) wherein at least one of said one or more cellulase enzyme(s) is a CBH1, CBH2 or a BGL1; wherein said enzyme composition comprises a ratio of a about 0.5 to about 1.0 xylanases to cellulases (w/w) or a ratio of about 0.05 to about 1.5 xylanase to CBH1 (w/w). In some embodiments, the enzyme composition comprises a ratio of about 0.1 to about 1.0 XYN2 to CBH1 (w/w). In some embodiments, the enzyme composition comprises a ratio of about 0.05 to about 0.5 XYN3 to CBH1 (w/w). In another embodiment, the enzyme composition comprises a ratio of about 0.05 to about 1.5 xylanase to CBH1 (w/w).

Yet another aspect of the teaching provides methods of degrading a biomass substrate comprising contacting the biomass with an enzyme composition induced by a mixed saccharide composition of the present disclosure. In the methods of the present disclosure, biomass substrate can be any biomass material containing both cellulose and hemicellulose. In some embodiments, the biomass substrate includes, but is not limited to, herbaceous material, agricultural residues, forestry residues, municipal solid waste, waste paper, and pulp and paper residues. Common forms of biomass substrate for use in the methods described herein include, but are not limited to trees, shrubs and grasses, wheat, wheat straw, sugar cane bagasse, corn, corn husks, corn kernel including fiber from kernels, products and by-products from milling of grains such as corn (including wet milling and dry milling) as well as municipal solid waste, waste paper and yard waste. The biomass substrate may be obtained from "virgin biomass" (such as trees, bushes, grasses, fruits, flowers, herbaceous crops, hard and soft woods.), "non-virgin biomass" (such as agricultural byproducts, commercial organic waste, construction and demolition debris, municipal solid waste and yard waste), or "blended biomass," which is a mixture of virgin and non-virgin biomass In some embodiments, the biomass substrate includes wood, wood pulp, papermaking sludge, paper pulp waste streams, particle board, corn stover, corn fiber, rice, paper and pulp processing waste, woody or herbaceous plants, fruit pulp, vegetable pulp, pumice, distillers grain, grasses, rice hulls, sugar cane bagasse, cotton, jute, hemp, flax, bamboo, sisal, abaca, straw, corn cobs, distillers grains, leaves, wheat straw, coconut hair, algae, switchgrass, and mixtures thereof.

The biomass substrate can be used directly or may be subjected to pretreatment using conventional methods known in the art. Such pretreatments include chemical, physical, and biological pretreatment. For example, physical pretreatment techniques can include without limitation various types of milling, crushing, steaming/steam explosion, irradiation and hydrothermolysis. Chemical pretreatment techniques can include without limitation dilute acid, alkaline, organic solvent, ammonia, sulfur dioxide, carbon dioxide, and pH-controlled hydrothermolysis. Biological pretreatment techniques can include without limitation applying lignin-solubilizing microorganisms.

Optimum dosage levels of enzyme composition, vary depending on the biomass substrate and the pretreatment technologies used. Operating conditions such as pH, temperature and reaction time may also affect rates of biomass degradation. Preferably, the reactive composition contains 0.1 to 200 mg enzyme composition per gram of biomass substrate, more preferably 1 to 100 mg enzyme composition per gram of biomass substrate and most preferably 3 to 25 mg enzyme composition per gram of biomass substrate. Exemplary amounts are 0.1-50, 1-40, 20-40, 1-30, 2-40, and 10-20 mg enzyme composition per gram of biomass. Alternatively, the amount of enzyme can be determined based on the amount of substrate in the system. In such a case, the reactive composition preferably contains 0.1 to 50 mg enzyme composition per gram of total saccharides, more preferably, 1 to 30 mg enzyme composition per gram of total saccharides, and more preferably 5 to 20 mg enzyme composition per gram of total saccharides. Alternatively, the amount of enzyme can be determined based on the amount of cellulose substrate in the system. In such a case, the reactive composition preferably contains 0.2 to 100 mg enzyme composition per gram of total glucan, more preferably, 2 to 60 mg enzyme composition per gram of total glucan, and more preferably 10 to 40 mg enzyme composition per gram of total glucan. Similarly, the amount of enzyme composition utilized can be determined by the amount of xylan in the substrate biomass. Accordingly, the reactive composition preferably contains 0.2 to 100 mg enzyme composition per gram of xylan, more preferably, 2 to 60 mg enzyme composition per gram of xylan, and more preferably 10 to 40 mg enzyme composition per gram of xylan.

One aspect of the present disclosure provides enzyme compositions that have substantial amounts of both cellulase and xylanase and are produced according to the methods described herein. In a preferred implementation, the enzyme composition comprises cellulase in the range of 80% to 98% of the total protein and xylanase the range of 2% to 20% of total protein. In one embodiment, xylanase represents greater than 2% of the total protein, preferably greater than about 5% of the total protein and most preferably greater than about 20% of total protein. In another embodiment, cellulase represents greater than 50% of the total protein, more preferably greater than about 75% of the total protein and most preferably greater than about 80% of total protein.

Other aspects and embodiments of the compositions and method may be further understood in view of the following examples, which should not be construed as limiting. It will be apparent to those skilled in the art that many modifications, both to materials and methods, may be made without departing from the present teachings.

VI. EXAMPLES

A. Example 1

Production of Mixed Saccharide Composition

A 71% (w/w) glucose solution was added to an empty fermentor tank. A cellulase preparation over-expressing β-glucosidase (Accellerase BG, Danisco) was added to the glucose solution to a final concentration of 0.0357MU β-glu activity/Kg glucose syrup. The tank containing the glucose and cellulase mixture was held at 65° C. and pH 5.0 for 3 days with gentle mixing. Following incubation, the solution was sterilized at 121° C. for 30 minutes and harvested to an appropriate container for fermentation feeding. The resulting processed glucose solution was found to have decreased in glucose concentration from 740 g/Kg to 570 g/Kg. Xylose sugar was added to some lots from this processed glucose solution to a concentration of 15 g/L to generate a mixed saccharide composition.

B. Example 2

Production of Enzyme Composition 0.8 L of media was inoculated with 1.5 ml *Trichoderma reesei* frozen spore suspension as a seed flask. This flask was split into two 0.4 L portions and transferred to 2×7 L of fermentation media in two different 15 L Biolafitte fermentors after 48 hours. The growth media had the following composition (Table 1):

TABLE 1

| Media component | g/L |
|---|---|
| $KH_2PO_4$ | 4 |
| $(NH_4)2SO_4$ | 6.35 |
| $MgSO_4$—$7H_2O$ | 2 |
| $CaCl_2$—$2H_2O$ | 0.53 |
| Glucose | 80 |
| Corn Steep Solids | 6.25 |

TABLE 1-continued

| Media component | g/L |
|---|---|
| (Roquette) Trace elements* | 1 ml/L |

Trace elements: 5 g/L $FeSO_4$-$7H_2O$; 1.6 g/L $MnSO_4$—$H_2O$; 1.4 g/L $ZnSO_4$-$7H_2O$.

The fermentor was run at 25 or 30° C., 750 RPM, 0.3 g sugar feed/min and 8 standard liters per minute (SLM) airflow. After inoculation of the fermentor from a flask, the cells will go through batch growth for the first 18-24 hours. After the batched glucose is exhausted, the glucose feed is started at 0.3 g/minute and continues for the next 180 hours.

In this set of fermentation experiments pH was varied between 4.8 and 5.5, Temperature was varied between 25 and 30° C., and 15 g/L Xylose was added to the transglycosylated glucose solution in some cases (indicated by a '+' in Table 2).

TABLE 2

| lot | pH | Temp (° C.) | Xylose |
|---|---|---|---|
| 1 | 4.8 | 25 | − |
| 2 | 5.5 | 25 | − |
| 3 | 4.8 | 30 | − |
| 4 | 5.5 | 30 | − |
| 5 | 4.8 | 25 | + |
| 6 | 5.5 | 25 | + |
| 7 | 4.8 | 30 | + |
| 8 | 5.5 | 30 | + |

The whole broth of each fermentation run was analyzed for hemicellulase and cellulase enzymes activities. The endoglucanase activity of each enzyme preparation was quantified using carboxymethyl cellulose (CMC) as substrate (Ghose, "Measurement of Cellulase Activities" *Pure & Appl. Chem.*, 1987, 59(2), 257-268). The β-glucosidase activity of each enzyme preparation was quantified using p-nitrophenyl β-D-1,4-glucopyranoside (pNPG) as substrate (Chen, et al. "Purification and characterization of two extracellular β-glucosidases from *Trichoderma reesei*," *Biochimica et Biophysica Acta*, 1992, 1121, 54-60). Similarly, the endoxylanase activity was quantified following Acid Birchwood Xylanase (ABX) assay using 4-O-methylglucuronic xylan (birch wood) as substrate (Bailey, "Interlaboratory testing off methods for assay of xylanase activity." *J. Biotechnol.*, 1992, 23, 257-270), and the β-xylosidase Activity was quantified using 4-Nitrophenyl β-D-xylopyranoside (pNPX) as substrate (Cleemput, et al., "Purification and characterization of a β-xylosidase and an endo-xylanase from wheat flour." *Plant Physiol.* 1997, 113, 377-386).

The different cellulase (CMCU/g), xylanase (ABXU/g), β-glucosidase (pNPGU/g) and β-xylosidase (pNPXU/g) activities are shown in Table 3. Xylanase (ABXU) and β-xylosidase (pNPX) activities varied greatly from condition to condition, while the CMC and pNPG activities were quite similar. This indicates that, hemicellulase production was significantly enhanced at most of the conditions, while cellulase production was not seriously impacted.

Total Protein produced was similar in all cases with the pH 5.5 condition producing slightly less than the pH 4.8 condition (15-20% reduction).

TABLE 3

| pH | temp (° C.) | Xylose | Total protein (g/L) | Endogluc. (CMCU/g) | β-glucos. (pNPGU/g) | Endoxyl. (ABXU/g) | β-xylosid. (pNPXU/g) |
|---|---|---|---|---|---|---|---|
| 4.8 | 25 | − | 62.57 | 2843 | 1657 | 826 | 3.31 |
| 4.8 | 25 | + | 66.70 | 2767 | 1439 | 2386 | 5.67 |
| 4.8 | 30 | − | 61.83 | 2737 | 1626 | 1184 | 6.19 |
| 4.8 | 30 | + | 55.83 | 2524 | 1637 | 3340 | 1.06 |
| 5.5 | 25 | − | 59.77 | 2300 | 1366 | 1277 | 2.04 |
| 5.5 | 25 | + | 56.30 | 2371 | 1184 | 7597 | 7.7 |
| 5.5 | 30 | − | 50.50 | 1813 | 1119 | 1514 | 5.43 |
| 5.5 | 30 | + | 50.60 | 1499 | 780 | 2279 | 6.14 |

C. Example 3

Components of Enzyme Composition

The significant difference in hemicellulase production can be seen by comparing the HPLC profile of these fermentation samples.

The major components of mixed cellulase compositions, including CBH1, CBH2, BGL11, XYN2, and XYN3, were separated utilizing HPLC Reverse Phase Chromatography. Table 4 provides the relative peak height of these components normalized to the corresponding peak height of the control conditions (pH 4.8, 25° C.). Expression of XYN2 and XYN3 were enhanced up to 4 folds under the conditions tested in this experiment, while the expression of CBH1, CBH2 and BGL1 did not change much under the conditions tested.

TABLE 4

| pH | temp | Xylose | CBH1 | CBH2 | Bgl1 | Xyn3 | Xyn2 |
|---|---|---|---|---|---|---|---|
| 4.8 | 25 | − | 1 | 1 | 1 | 1 | 1 |
| 4.8 | 25 | + | 0.86 | 1.02 | 0.91 | 2.19 | 2.15 |
| 4.8 | 30 | − | 0.94 | 0.88 | 0.92 | 1.1 | 1.6 |
| 4.8 | 30 | + | 0.87 | 0.8 | 0.85 | 1.7 | 3.21 |
| 5.5 | 25 | − | 0.82 | 0.81 | 0.91 | 2.28 | 1.35 |
| 5.5 | 25 | + | 0.82 | 0.83 | 0.81 | 4.2 | 3.16 |
| 5.5 | 30 | − | 0.85 | 0.82 | 0.86 | 1.63 | 2.37 |
| 5.5 | 30 | + | 0.79 | n.d. | 0.83 | 1.86 | 4.88 |

The HPLC results agreed well with the activity assay shown in Table 3. Xylanase production was significantly enhanced at most of the conditions, while cellulase production was not substantially impaired.

D. Example 4

Production of Enzyme Composition

The processed glucose solution was prepared as described in Example 1, above. *Trichoderma reesei* was prepared for fermentation in the growth medium of Table 1, as described in Example 2.

The fermentor was run at 25° C., 750 RPM, 0.3 g sugar feed/min and 8 standard liters per minute (SLM) airflow. After inoculation of the fermentor from a flask, the cells will go through batch growth for the first 18-24 hours. After the batched glucose is exhausted, the glucose feed is started at 0.3 g/minute and continues for the next 180 hours.

In this set of fermentation experiments pH was varied between 4.4 and 5.5, Temperature was fixed at 25° C., and Xylose added to the transglycosylated glucose solution varied between 5 g/L and 15 g/L as indicated in Table 5.

TABLE 5

| lot | pH | Temp (° C.) | Xylose |
|---|---|---|---|
| 1 | 5.5 | 25 | 15 |
| 2 | 5.5 | 25 | 5 |
| 3 | 4.4 | 25 | 15 |

The whole broth of each fermentation run was analyzed for xylanase activities. The endoxylanase activity was quantified following Acid Birchwood Xylanase (ABX) assay using 4-O-methylglucuronic xylan (birch wood) as substrate (Bailey, "Interlaboratory testing off methods for assay of xylanase activity." *J. Biotechnol.*, 1992, 23, 257-270). As shown in Table 6, Xylanase (ABXU) activities varied greatly from condition to condition, This indicates that, hemicellulase production was significantly enhanced at most of the conditions, even with only 5 g/L of xylose in feed.

Total Protein produced was similar in all cases with the pH 4.4 condition producing slightly less than the pH 5.5 condition (10% reduction).

TABLE 6

| pH | temp (° C.) | Xylose (g/L) | Total protein (g/L) | Endoxyl. (ABXU/g whole broth) |
|---|---|---|---|---|
| 5.5 | 25 | 15 | 71.6 | 3669 |
| 5.5 | 25 | 5 | 71.0 | 3853 |
| 4.4 | 25 | 15 | 64.1 | 1157 |

E. Example 5

Components of Enzyme Composition

A significant difference in hemicellulase production can be seen by comparing the HPLC profile of these fermentation samples. The major components of mixed cellulase compositions, including CBH1, CBH2, BGL1, XYN2, and XYN3, were separated utilizing HPLC Reverse Phase Chromatography. Table 7 provides the relative peak area of these components normalized to the total peak area of all the peaks detected (Integrated Area/Total Peak Area (%)). Both Xyn2 and Xyn3 were well expressed even at as low as 5 g/L xylose.

TABLE 7

| pH | temp | Xylose | CBH1 (%) | CBH2 (%) | Bgl1 (%) | Xyn3 (%) | Xyn2 (%) |
|---|---|---|---|---|---|---|---|
| 5.5 | 25 | 15 | 42.3 | 22.8 | 12.8 | 2.7 | 6.0 |
| 5.5 | 25 | 5 | 40.0 | 25.2 | 12.9 | 2.0 | 6.3 |
| 4.4 | 25 | 15 | 53.3 | 24.7 | 10.9 | n.d. | 2.7 |

The HPLC results agreed well with the activity assay shown in Table 6. Xylanase production was significantly enhanced at most of the conditions.

F. Example 6

Production of Enzyme Composition

The processed glucose solution was prepared as described in Example 1, above. *Trichoderma reesei* was prepared for fermentation in the growth medium of Table 1, as described in Example 2.

The fermentor was run at 25° C., 750 RPM, 0.3 g sugar feed/min and 8 standard liters per minute (SLM) airflow. After inoculation of the fermentor from a flask, the cells will go through batch growth for the first 18-24 hours. After the batched glucose is exhausted, the glucose feed is started at 0.3 g/minute and continues for the next 180 hours.

In this set of fermentation experiments pH was varied between 4.8 and 5.5, Temperature was varied between 25 and 30° C., and 15 g/L Xylose was added to the transglycosylated glucose solution in some cases (indicated by a '+' in Table 8).

TABLE 8

| lot | pH | Temp (° C.) | Xylose |
|-----|-----|-------------|--------|
| 1 | 4.8 | 25 | + |
| 2 | 5.5 | 25 | + |
| 3 | 5.5 | 30 | + |
| 4 | 4.8 | 30 | + |
| 5 | 4.8 | 25 | − |

TABLE 9

| pH | temp (° C.) | Xylose | Total protein (g/L) | Endoxyl. (ABXU/g whole broth) |
|----|-------------|--------|---------------------|-------------------------------|
| 4.8 | 25 | + | 72.51 | 2334 |
| 5.5 | 25 | + | 57.06 | 3416 |
| 5.5 | 30 | + | 48.11 | 2784 |
| 4.8 | 30 | + | 66.49 | 2451 |
| 4.8 | 25 | − | 69.13 | 621 |

G. Example 7

Components of Enzyme Composition

The significant difference in hemicellulase production can be seen by comparing the HPLC profile of these fermentation samples. The major components of mixed cellulase compositions, including CBH1, CBH2, Bgl1, XYN2, and XYN3, were separated utilizing HPLC Reverse Phase Chromatography Table 10 provides the relative peak area of these components normalized to the total peak area of all the peaks detected (Integrated Area/Total Peak Area (%)). The concentration of hemicellulases (including both Xyn2 and Xyn3) in whole broth were enhanced up to 24% under the conditions tested, while the expression of CBH1, CBH2 and BGL1 did not change much under the conditions tested.

TABLE 10

| pH | Temp (° C.) | Xylose | CBH1 (%) | CBH2 (%) | Bglu1 (%) | Xyn3 (%) | Xyn2 (%) | Xyn2 + Xyn3 (%) | Xylanase increase (%) |
|----|-------------|--------|----------|----------|-----------|----------|----------|-----------------|-----------------------|
| 4.8 | 25 | + | 47.2 | 10.5 | 23.3 | 2.2 | 5.6 | 7.9 | 5.2 |
| 5.5 | 25 | + | 30.6 | 11.0 | 24.7 | 9.3 | 12.5 | 21.8 | 19.1 |
| 5.5 | 30 | + | 24.1 | 4.1 | 32.5 | 8.9 | 18.1 | 26.9 | 24.2 |
| 4.8 | 30 | + | 47.8 | 5.8 | 25.5 | 1.8 | 7.8 | 9.7 | 7.0 |
| 4.8 | 25 | − | 51.5 | 13.1 | 23.4 | 0.6 | 2.1 | 2.7 | N/A |

The whole broth of each fermentation run was analyzed for xylanase activities. The endoxylanase activity was quantified following Acid Birchwood Xylanase (ABX) assay using 4-O-methylglucuronic xylan (birch wood) as substrate (Bailey, "Interlaboratory testing off methods for assay of xylanase activity." J. Biotechnol., 1992, 23, 257-270). As shown in Table 9, Xylanase (ABXU) activities varied greatly from condition to condition, This indicates that hemicellulase production was significantly enhanced at most of the conditions with the addition of 15 g/L of xylose in the feed.

From Table 10, the fold increase in XYN2, XYN3 or xylanases (XYN2 and XYN3) was determined (Table 11). By calculating the ratio between Xyn2, Xyn3, or xylanases (XYN2+XYN3) and CBH1 one can see the wide range from 0.05 for the control condition with out xylose, to about 1.12 with xylose (see Table 11). By calculating the ratio between Xyn2, Xyn3, and xylanases (Xyn2 and Xyn3) relative to cellulases (CBH1 and CBH2 and Bgl1), one can see the wide range from 0.03 for the control condition without xylose, to about 0.44 with xylose (see Table 11).

TABLE 11

| pH | Temp (° C.) | Xylose | Fold XYN2 increase | Fold XYN3 increase | Fold Xylanase increase | Ratio XYN2 to CBH I | Ratio XYN3 to CBH I | Ratio Xylanases to CBHI | Ratio Xylanases to Cellulases |
|---|---|---|---|---|---|---|---|---|---|
| 4.8 | 25 | + | 1.6 | 2.6 | 1.9 | 0.12 | 0.05 | 0.17 | 0.10 |
| 5.5 | 25 | + | 5.0 | 14.5 | 7.1 | 0.4 | 0.3 | 0.71 | 0.33 |
| 5.5 | 30 | + | 7.6 | 13.8 | 8.9 | 0.75 | 0.37 | 1.12 | 0.44 |
| 4.8 | 30 | + | 2.7 | 2.0 | 2.6 | 0.16 | 0.04 | 0.20 | 0.12 |
| 4.8 | 25 | − | N/A | N/A | N/A | 0.04 | 0.01 | 0.05 | 0.03 |

The invention claimed is:

1. A method for preparing a mixed saccharide composition, said method comprising:
   a) mixing a glucose solution with a transglycosylating enzyme to give an enzyme-glucose mixture;
   b) incubating the enzyme-glucose mixture at an elevated temperature of 50° C. to 75° C. for a time sufficient to give a processed glucose mixture comprising at least one oligosaccharide; and
   c) mixing the processed glucose mixture with a pentose to yield the mixed saccharide composition,
wherein the transglycosylating enzyme is capable of processing the glucose in the glucose mixture into at least one oligosaccharide, which, when mixed with the pentose of c), is capable of enhancing hemicellulase production without significantly reducing cellulase production by filamentous fungi.

2. The method of claim 1 wherein the glucose solution comprises 5% to 75% (wt/wt) glucose.

3. The method of claim 1, wherein the transglycosylating enzyme is β-glucosidase.

4. The method of claim 1, wherein the transglycosylating enzyme is an endoglucanase.

5. The method of claim 1 wherein the enzyme-glucose mixture is incubated for between 8 hours and 500 hours.

6. The method of claim 1, wherein the pentose is xylose.

7. The method of claim 6, wherein the concentration of xylose in the mixed saccharide composition is 1 g/L to 50 g/L.

8. A method for preparing an enzyme composition, comprising
   a) mixing a glucose solution with a transglycosylating enzyme to give an enzyme-glucose mixture;
   b) incubating the enzyme-glucose mixture at an elevated temperature of 50° C. to 75° C. for a time sufficient to give a processed glucose mixture comprising at least one oligosaccharide;
   c) mixing the processed glucose mixture with a pentose to yield a mixed saccharide composition; and
   d) exposing a filamentous fungi to the mixed saccharide composition under conditions conducive to protein expression to generate the enzyme composition,
wherein the transglycosylating enzyme is capable of processing the glucose in the glucose mixture into at least one oligosaccharide, which, when mixed with the pentose of c), is capable of enhancing hemicellulase production without significantly reducing cellulase production by filamentous fungi.

9. The method of claim 8, wherein the enzyme composition comprises 70% to 98% cellulase and 2% to 30% xylanase.

10. The method of claim 8, wherein the conditions conducive to protein expression comprise a temperature of between 25° C. and 30° C.

11. The method of claim 8, wherein the conditions conducive to protein expression comprise acidic conditions of between pH 4.0 and 6.0.

12. The method of claim 8, wherein said enzyme composition comprises at least a 1.5-fold increase in xylanase as compared to an enzyme composition prepared without step c).

13. The method of claim 8, wherein said enzyme composition comprises at least a 1.5-fold increase in XYN2 as compared to an enzyme composition prepared without step c).

14. The method of claim 8, wherein said enzyme composition comprises at least a 1.5-fold increase in XYN3 as compared to an enzyme composition prepared without step c).

15. The method of claim 8, wherein said enzyme composition comprises a ratio of 0.05 to 1.5 xylanase to CBH1 (wt/wt).

16. The method of claim 8, wherein said enzyme composition comprises a ratio of 0.1 to 1.0 XYN2 to CBH1 (wt/wt).

17. The method of claim 8, wherein said enzyme composition comprises a ratio of 0.05 to 0.5 XYN3 to CBH1 (wt/wt).

18. The method of claim 8, wherein said enzyme composition comprises a ratio of 0.5 to 1.0 xylanases to cellulases (wt/wt).

19. The method of claim 18, wherein said xylanases comprises XYN2 and XYN3.

20. The method of claim 18, wherein said cellulases comprises CBH1, CBH2 and BGL1.

* * * * *